United States Patent [19]

James et al.

[11] Patent Number: 5,062,432

[45] Date of Patent: Nov. 5, 1991

[54] METHOD AND APPARATUS FOR MONITORING PERSONAL CORE TEMPERATURE

[75] Inventors: Paul James, Marietta, Ga.; Theodore J. Kuemmel, Waukesha, Wis.; Michael G. Wurm, Franklin, Wis.; James D. Banach, Milwaukee, Wis.; David Fulton, Pickering, Canada

[73] Assignee: LaBelle Industries, Inc., Oconomowoc, Wis.

[21] Appl. No.: 521,088

[22] Filed: May 9, 1990

[51] Int. Cl.⁵ .............................................. A61B 5/00
[52] U.S. Cl. ................................................... 128/736
[58] Field of Search ................... 128/736; 374/158; 181/129

[56] References Cited

U.S. PATENT DOCUMENTS

| | | |
|---|---|---|
| 1,729,303 | 9/1929 | von Baussen ........................ 181/129 |
| 3,274,994 | 9/1966 | Sturm ................................... 128/736 |
| 3,933,045 | 1/1976 | Fox et al. ............................. 128/736 |
| 4,116,228 | 9/1978 | Hudspeth et al. .................... 128/736 |
| 4,191,197 | 3/1980 | Benzinger ............................ 128/736 |
| 4,407,295 | 10/1983 | Steuer et al. ....................... 128/670 |
| 4,819,860 | 4/1989 | Hargrove et al. ................... 128/736 |
| 4,862,509 | 8/1989 | Towsend .............................. 381/163 |
| 4,904,997 | 2/1990 | Chen et al. ........................ 340/870.17 |

Primary Examiner—William E. Kamm
Assistant Examiner—Kevin Pontius
Attorney, Agent, or Firm—Michael, Best & Friedrich

[57] ABSTRACT

A personal temperature monitor senses inner ear temperature and uses the sensed ear temperature to determine the internal core body temperature. The monitor places an audible signal device at the ear of the individual being monitored to alert the person when elevating core body temperatures may be indicative of a potentially dangerous heat stress condition.

20 Claims, 2 Drawing Sheets

METHOD AND APPARATUS FOR MONITORING PERSONAL CORE TEMPERATURE

This invention relates to a method of temperature monitoring and devices for achieving same and, more particularly, to such a method and device which monitors the internal core temperature of a person in an environment which poses a potential for dangerous heat stress.

BACKGROUND OF THE INVENTION

The potential for injury to individuals operating for prolonged periods in an abnormal temperature environment is well recognized and has been for a considerable period of time. Individuals such as steel mill and power plant workers, firefighters, and heavy machine operators perform duties in such environments and are exposed to considerable risk of illness and/or injury due to heat stress. These particular environments involve elevated temperatures, but exposure to undue low temperatures can also result in problems, for example hypothermia.

Past efforts to protect against such heat stress have included monitoring the environmental condition per se, that is the ambient temperature, radiant heat, humidity, etc.

It has been recognized that internal body core temperature is an accurate parameter for assessing heat stress. Continuous monitoring of the internal core temperature by means of a rectal thermometer has been proposed. In addition, there have been efforts to use skin temperature and heart rate as parameters in assessing internal core temperature.

These prior approaches have various shortcomings in that they are uncomfortable, difficult to use, and/or lack reliability and accuracy.

Among the objects of this invention are to provide accurate, reliable, easy-to-use, and/or physically unobtrusive monitoring of internal core temperature.

SUMMARY OF THE INVENTION

For the achievement of these and other objects, this invention proposes monitoring the core temperature of a living being by determining the difference between ear canal and oral temperature in a normal environment and then continuously monitoring the ear canal temperature and extrapolating the inner core temperature from the monitored ear canal temperature and using the initially determined temperature difference between the ear canal temperature and the oral temperature. Preferably, the monitoring of the ear canal temperature is accomplished by a temperature sensor in the ear canal.

The apparatus for carrying out this method includes a temperature monitor adapted to be positioned in the ear canal of the person being monitored. The apparatus further includes means for receiving a signal from the ear canal monitor and from a second temperature sensor that can be located in an orifice of the person being monitored. That receiving means determines a first, predetermined difference between the ear canal temperature and the orifice temperature. The ear canal monitor continues to deliver signals to the signal receiving mechanism which then extrapolates the core temperature from the continuously monitored ear canal temperature utilizing the initially determined difference between ear canal temperature and orifice temperature.

Preferably, the apparatus also includes a visible and/or audible signal which is activated when the extrapolated core temperature exceeds a predetermined threshold temperature. In the preferred embodiment, the audible signal producing mechanism is supported in close association with the mechanism insertable into the ear canal so that it is positioned adjacent the ear being monitored.

Other objects and advantages will be pointed out in, or be apparent from, the following specification and claims as will obvious modifications of the embodiment shown in the drawings in which:

DESCRIPTION OF THE PREFERRED EMBODIMENT

Figure 1:
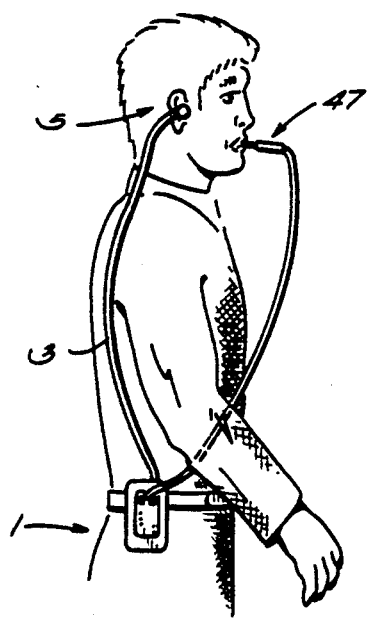
FIG. 1 is an illustration of a heat stress monitor as worn by an individual.
Figure 2:
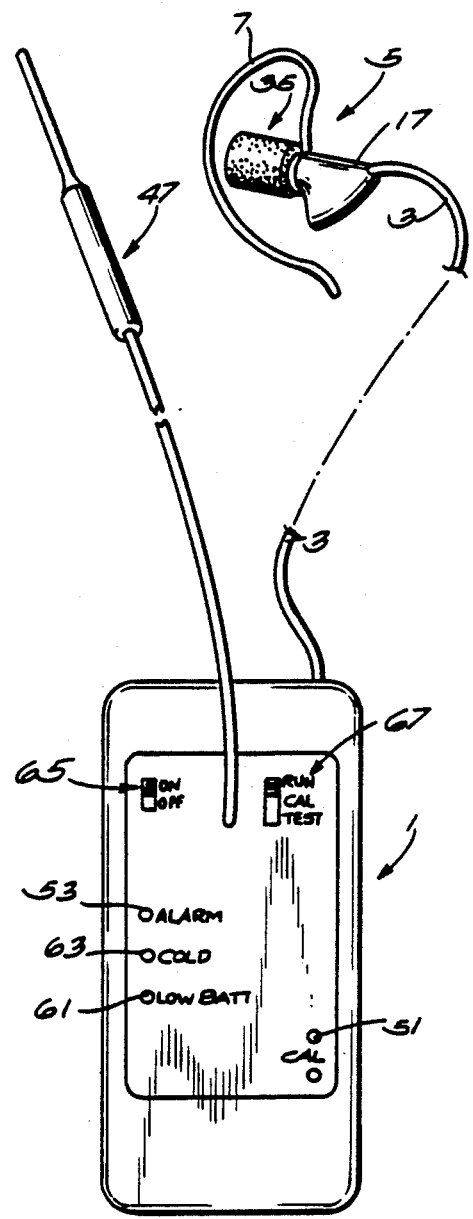
FIG. 2 is an illustration of the packaged heat stress monitor.

With particular reference to FIG. 1, the power pack/electronic assembly unit 1 is illustrated as hanging from the belt of a worker. The attachment to the worker's belt is by any conventional mechanism (not shown). A cable 3 extends from the unit 1 to the worker's ear. The cable 3 connects with an earplug assembly 5 which is in turn attached to an ear clip 7. The ear clip is substantially in the form of a "D" and, in a conventional manner, fits over the worker's ear, i.e., the pinna, to position the earplug assembly 5 at the entry to ear canal.

Figure 3:
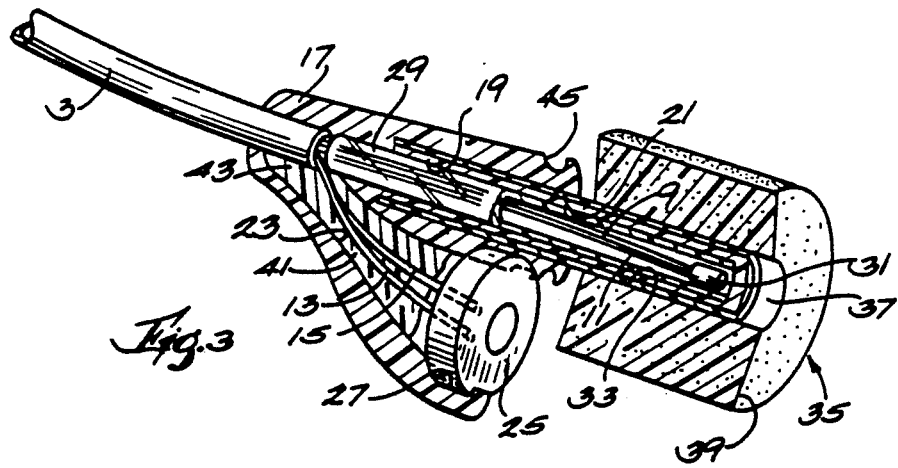
FIG. 3 is a cross section of the earplug assembly.

More specifically and with reference to FIG. 3, cable 3 contains two pairs of electrical leads 9, 11 and 13, 15. Leads 9 and 11 separate from leads 13 and 15 in the body 17 of the earplug assembly 5 and extend through a channel 19 to and through an opening 21. Leads 13 and 15 in turn extend into a channel 23 to a speaker, preferably a piezo buzzer, 25. Speaker 25 is supported in an annular groove 27 in body 17.

Leads 9 and 11 are enclosed in a tubular sheath 29 made from suitable electrical insulating material such as teflon. A temperature sensing device such as a thermistor 31 is attached to leads 9 and 11 and is exposed at the free outer end of sheath 29. The assembly of the thermistor leads and teflon sheath extend through a second tubular sheath 33 which separates the teflon sheath 29 from the walls of the housing 17. Tubular member 33 is also made of suitable electrical insulating material.

A sponge-like cylindrical member 35 surrounds the outer, otherwise exposed end of the leads 9 and 11 and teflon sheath 19. The material of the cylindrical member 35 is conventional and a typical product is sold by the Cabot Corporation of Indianapolis, Indiana under the registered trademark E.A.R. Plug. The cylindrical member 35 contains a cylindrical bore 37 and is positioned over the thermistor so that the thermistor is axially spaced inwardly of the end 39 of the cylindrical member 35, preferably in the neighborhood of 1/10 of a inch.

A suitable epoxy compound is potted into the earplug body 17 at areas 41 and 43 to anchor the leads 13, 15 and 9, 11 in the earplug body 17. This forms a unitary, stress relieved connection for the electrical leads.

The ear loop 7 fits into a groove 45 in the earplug body 17.

With the structure just described, when the cylindrical member 35 is placed in the ear, it seals the ear canal chamber from the outer environment. This sealing is generally accomplished by squeezing or rolling the cylindrical member 35 to reduce its diameter, inserting the cylindrical member 35 into the ear canal while the cylindrical member 35 is still in that compressed state and then releasing the cylindrical member 35 so that it can expand against the inner ear walls. Once so isolated from the outer environment, the thermistor is exposed to and accurately monitors the ear canal temperature, i.e., the temperature adjacent or in the area of the tympanic membrane. The thermistor being spaced inwardly from the end of cylindrical member 35 protects the user from over-extension of the thermistor into the ear canal which could, under abnormal circumstances, engage and possibly contact the eardrum. When the cylindrical member 35 is inserted into the ear canal, the speaker 25 is proximate to, but external of, the ear canal.

As stated previously, this device is intended to provide a continuous monitoring of the internal body core temperature for workers who are exposed in a high temperature, and correspondingly potentially hazardous, environment. It makes use of the concept that the temperature in the ear canal is a reliable indication of the body core temperature. It has been found that for each individual there is a predictable differential between the ear canal temperature and the body's core temperature. This differential may vary from person to person, but will remain relatively constant for an individual as that person is exposed to elevated temperatures and the body core temperature increases. Thus, when the inner core temperature becomes elevated, the ear canal temperature will be correspondingly elevated. By sensing the amount that ear canal temperature is elevated from a given predetermined temperature, an increase in the level of the body core temperature can be determined. It has been recognized that increases in core temperature above 38° C. (100.4° F.) will expose an individual to risk of injury or illness. Orifice temperature, i.e., oral or rectal temperature, substantially corresponds to body core temperature.

Many workers who perform duties in environments mentioned above may well use enclosed protective suits and thereby may be further exposed to danger of overheating because of heat stress. In addition, because the workers are enclosed in such suits, external temperature monitoring devices would not be reliable either from an actual body temperature sensing standpoint or from the standpoint of providing a readily available signal of elevated temperatures to the worker.

With the device of this invention, the worker inserts the cylindrical member 35 into his or her ear canal, and supports the power pack unit, if such a protective suit is worn, within that suit. The audible signal which will be provided by the speaker 25 is right at the worker's ear for effective warning and response.

In operation, the worker inserts the cylindrical member 35 into his or her ear canal. The worker then, after a sufficient time to allow the thermistor to have sensed the ear canal temperature, places an oral probe, an electronic thermometer 47, into his or her mouth. The oral probe 47 connects to the unit through a jack connection shown schematically in FIG. 4. Memory means are provided for storing the difference between ear canal temperature and orifice temperature. In the illustrated embodiment, the memory means includes a calibrating screw 49 connected to a variable resistor 59 as described below. The memory means could alternatively include solid state volatile or non-volatile electronic memory.

Figure 4:
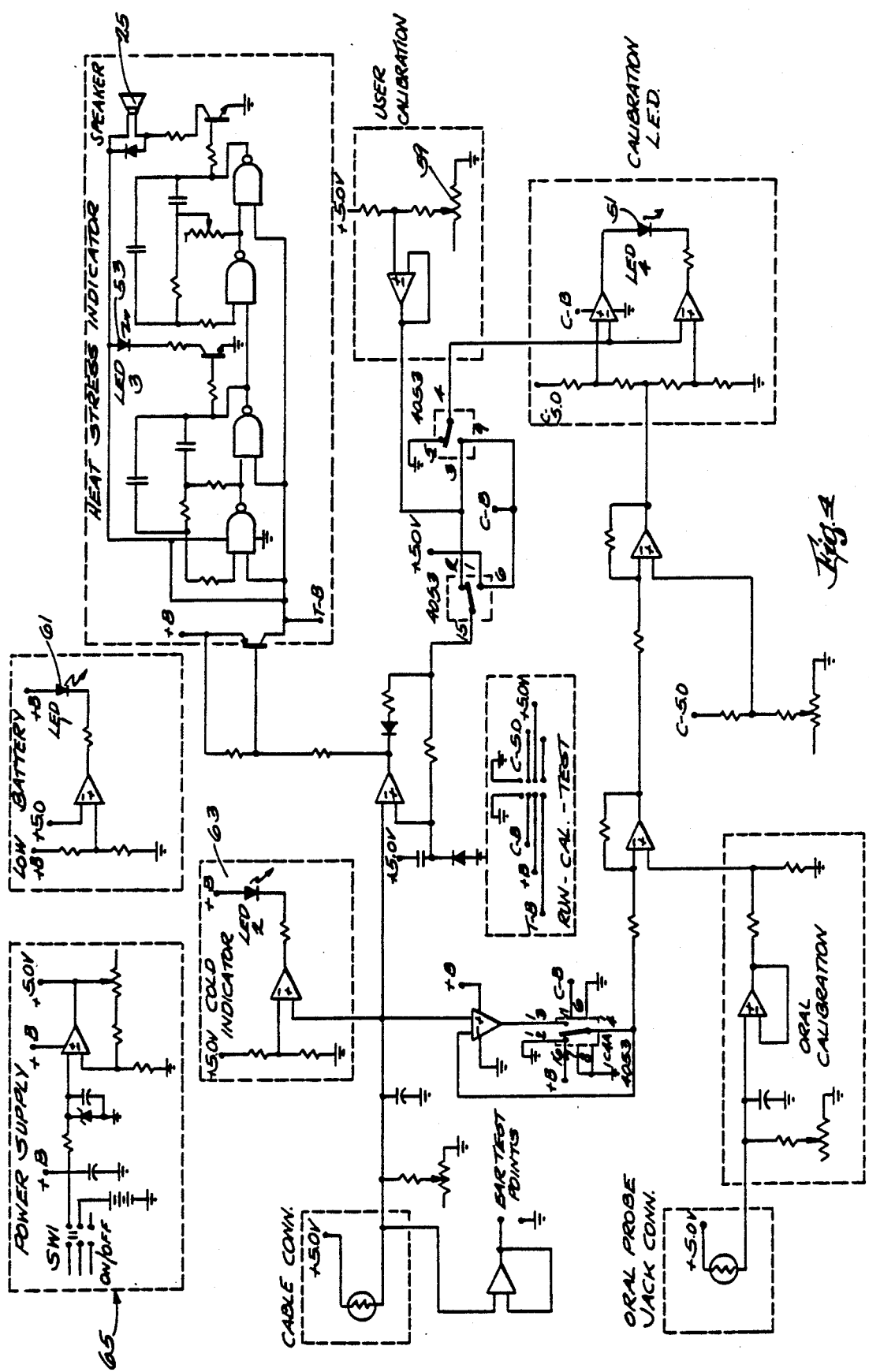
FIG. 4 is a circuit diagram for the electronic workings of the heat stress monitor.

The temperature signal from the oral probe is fed to the circuitry illustrated in FIG. 4, which already has registered the ear canal temperature. After a sufficient time to allow the oral probe to stabilize, the worker turns the calibrating screw until a light, which is preferably a light emitting diode, 51, in the calibration portion of the circuit of the unit 1 turns on. This then tells the worker that the unit has been properly calibrated, i.e., the difference between that worker's ear canal temperature and the inner core temperature has been fed to and stored within the unit 1. Once the calibration has been established, the oral probe can be set aside and the worker can go about his or her duties in the hazardous environment.

Typically, there is a differential between the true inner core temperature and the temperature which is sensed orally, that differential is generally in the neighborhood of 0.4° C. An "alarm level" is predetermined in the unit 1 by using the accepted upper core temperature of 38° C., the typical differential between oral and inner core temperature, and the difference between the orally sensed temperature and the ear canal temperature. That level is determined by the equation 38° C.−(0.4° C.)−(oral temperature (° C.)−ear temperature (° C.))=alarm level (° C.).

In humans, the differential between the ear canal temperature and the oral temperature (which corresponds substantially to body core temperature) remains relatively constant as ear canal temperature increases. That is, although the ear canal temperature may increase, the differential between it and the inner core will remain constant. Therefore, a unit continually sensing the ear canal temperature gives an accurate parameter for use in determining inner core temperature. The circuit of the electronic assembly 1 (FIG. 4) which receives and stores the differential between the ear canal temperature and the oral temperature, extrapolates in real-time from the sensed ear canal temperature to produce a calculated inner core temperature. When that calculated inner core temperature exceeds a predetermined threshold, the alarm level, a signal activates a visual indicator, which is preferably a light emitting diode, 53, on the unit 1 and activates the speaker 25 to create a buzzing sound at the user's ear.

With reference to FIG. 4, the basic operational portions of the electronic circuit of the assembly 1 have been labeled.

More specifically, the POWER SUPPLY is shown in the upper lefthand corner. The oral probe 47 is introduced into the electronic circuit of the assembly 1 via the ORAL PROBE JACK CONNECTION. Calibration (i.e., storing of the differential between the ear canal temperature and oral temperature) is achieved through the USER CALIBRATION portion of the circuit. The USER CALIBRATION circuit is suitably connected to the calibration light emitting diode 51 and includes a variable resistance 59. Variable resistance 59 is the circuit element manipulated by the calibrating screw 49 to achieve calibration.

The HEAT STRESS INDICATOR is illustrated in the upper righthand corner of FIG. 4. The difference between the oral and ear temperatures and the continually monitored ear temperature is fed to the HEAT STRESS INDICATOR which then operates as described above. The HEAT STRESS INDICATOR contains the speaker 25 and light emitting diode 53. A LOW BATTERY INDICATOR circuit is also included with the light emitting diode 61 being illuminated when the battery charge has run down.

Although the invention has been described in connection with elevated temperatures, it can also be used to monitor when the worker is being exposed to reduced temperatures with potential hazards such as hypothermia. Means for sensing these lower temperatures can be included in the HEAT STRESS INDICATOR portion of the circuitry. However, in the illustrated embodiment, this means is included in the COLD INDICATOR, which is shown as part of the overall circuitry of the assembly 1. The COLD INDICATOR functions to warn the worker through a light emitting diode 63 when the ear sensor is sensing a temperature below a given threshold. As ambient temperature will be lower than the threshold ear canal temperature, the COLD INDICATOR will also function to indicate to the worker that the earplug assembly 5 has become disengaged from the ear canal and, therefore, is not sensing the ear canal temperatures but is being exposed to a lower, exterior temperature.

The on/off power switch 65 is illustrated as part of the POWER SUPPLY portion of the circuit. The selector switch 67 which has a run/calibration/test capability is shown in the middle of FIG. 4. The terminals for the run/calibration/test switch 67 have been labeled T-B (battery), +−B, C-B, C−5.0 and +5.0 V, as have other terminal points within the circuit to show how the switch and the various circuit elements are interconnected.

With the above functional description and the circuit diagram of FIG. 4, one skilled in the art will understand the actual functioning of the circuitry and, therefore, a detailed description of all of the circuit components will not be made.

Although this invention has been illustrated and described in connection with a particular embodiment thereof, it will be apparent to those skilled in the art that various changes and modifications may be made therein without departing from the spirit of the invention or from the scope of the appended claims.

We claim:

1. A method of monitoring the core temperature of a warm blooded living being, said method comprising the following steps in order:
   determining the difference between ear canal and orifice temperature of the being at a given instant of time;
   monitoring ear canal temperature of the being over time; and
   extrapolating inner core temperature at a given instant of time different from the first mentioned given instant of time as a function of the ear canal temperature at the second given instant of time and the determined difference.

2. A method in accordance with claim 1 and further comprising, prior to said determining step, the step of inserting a temperature sensor into the ear canal of the living being in such a fashion that the temperature sensor is generally isolated from the ambient of the living being.

3. A method in accordance with claim 1 and further comprising, after said extrapolating step, the step of comparing the extrapolated inner core temperature to at least one predetermined threshold temperature.

4. An apparatus for monitoring the core temperature of a warm blooded living being, said apparatus comprising:
   means for monitoring temperature in the ear canal of the living being;
   means for receiving an electronic signal from an orifice temperature sensor, the signal being representative of the core temperature of the living being at a given instant of time;
   means for determining the difference between the ear canal temperature and the orifice temperature at the given instant of time; and
   means for extrapolating the core temperature of the living being, at a second given instant of time different from the first mentioned instant of time, by using the monitored ear canal temperature at the second given instant of time and the determined difference.

5. An apparatus in accordance with claim 4 and further including means for comparing the extrapolated temperature to a predetermined threshold temperature.

6. An apparatus in accordance with claim 5 and further including means for generating a visible signal in response to the extrapolated temperature exceeding predetermined threshold.

7. An apparatus in accordance with claim 5 and further including means for generating an audible signal in response to the extrapolated temperature exceeding the predetermined threshold.

8. An apparatus in accordance with claim 5 and further including means for comparing the extrapolated temperature to a second predetermined threshold temperature lower than the first mentioned predetermined threshold temperature.

9. An apparatus in accordance with claim 8 and further including means for generating a visible signal in response to the extrapolated temperature falling below the second predetermined threshold temperature.

10. An apparatus in accordance with claim 4 wherein said temperature monitoring means comprises means insertable into a ear canal of a warm blooded living being for producing an electrical signal indicative of the temperature of the ear canal, wherein said apparatus further comprises selectively engageable means for producing an audible signal exterior of the ear canal, and wherein said selectively engageable means is structurally connected to said insertable means.

11. An apparatus in accordance with claim 10 and further including a body supporting said electrical signal producing means and supporting said selectively engageable means for at least generally common movement with said electrical signal producing means, said insertable means extending from said body for insertion into the ear canal, said body being of sufficiently large dimension to be non-insertable into the ear canal so as to limit insertion of said insertable means to a predetermined amount of insertion in the ear canal, said insertable means being configured so as to not contact the tympanic membrane when said insertable means is inserted into the ear canal by the predetermined amount of insertion.

12. An apparatus in accordance with claim 11 and further including means for supporting said body from the pinna of the living being with regard to the direction transverse of the axis of the ear canal.

13. An apparatus in accordance with claim 11 and further including
   a first pair of electrical conductors connected to said electrical signal producing means;
   a second pair of conductors connected to said audible signal producing means; and insulation surround a portion of both first and second pairs of conductors to define a signal cable extending from said body.

14. An apparatus in accordance with claim 13 wherein said second pair of conductors is potted to said body with epoxy, proximate said audible signal producing means, and wherein said insulation is potted to said body with epoxy.

15. An apparatus in accordance with claim 13 wherein said first pair of conductors and said electrical signal producing means are encased in a tubular, generally resilient non-conductive sheath, a portion of which extends from said body and a portion of which is encased by said body.

16. An apparatus in accordance with claim 15 and further including a generally cylindrical foam earpiece which is insertable into the ear canal, and which has a bore passing therethrough for sliding telescopic receipt of the portion of said tubular sheath which extends from said body.

17. An apparatus in accordance with claim 16 and further including a generally resilient hollow tube in said bore through said earpiece, and attached to said earpiece for close sliding telescopic receipt of at least the portion of said sheath which extends from said body.

18. An apparatus in accordance with claim 17 wherein said hollow tube includes a portion which extends from said earpiece, wherein said body defines a tubular recess surrounding at least a portion of said sheath for close telescopic receipt of said hollow tube portion which extends from said earpiece, while said hollow tube telescopically receives the portion of said sheath which extends from said body and the portion of said sheath surrounded by the tubular recess.

19. An apparatus in accordance with claim 10 wherein said electrical signal producing means is a thermistor.

20. An apparatus in accordance with claim 10 wherein said audible signal producing means is a piezo buzzer.

* * * * *